United States Patent [19]

Pasternak

[11] Patent Number: 5,139,677
[45] Date of Patent: Aug. 18, 1992

[54] MEMBRANE SEPARATION METHOD

[75] Inventor: Mordechai Pasternak, Spring Valley, N.Y.

[73] Assignee: Texaco Inc., White Plains, N.Y.

[21] Appl. No.: 793,899

[22] Filed: Nov. 18, 1991

[51] Int. Cl.$^5$ .............................................. B01D 61/37
[52] U.S. Cl. .................................... 210/640; 210/654
[58] Field of Search ........ 210/634, 640, 644, 649–654, 210/500.37, 500.38, 500.39; 55/158

[56] References Cited

U.S. PATENT DOCUMENTS 4,613,440  9/1986  Zupancic .............................. 55/158

Primary Examiner—Frank Sever
Attorney, Agent, or Firm—Robert A. Kulason; James J. O'Loughlin; Carl G. Seutter

[57] ABSTRACT

A solution of isopropanol or ethanol is concentrated by pervaporation across a membrane of polyurea polymer or polyamide polymer prepared by interfacial polymerization of (i) an amine monomer containing at least two primary or secondary amine nitrogens and (ii) an isocyanate monomer containing at least two —NCO groups or a carbonyl chloride monomer containing at least two —COCl groups.

17 Claims, No Drawings

MEMBRANE SEPARATION METHOD

FIELD OF THE INVENTION

This invention relates to a method of treating aqueous solutions. More particularly it relates to a membrane process for treating concentrated aqueous solutions to yield product characterized by decreased content of water.

BACKGROUND OF THE INVENTION

As is well known to those skilled in the art, it is possible to remove water from mixtures thereof with organic liquids by various techniques including adsorption or distillation. These conventional processes, particularly distillation, are however, characterized by high capital cost. In the case of distillation for example, the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs-principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, could require that operation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by reverse osmosis. In this process, the charge liquid is brought into contact with a membrane film; and one component of the charge liquid preferentially permeates the membrane. The permeate is then recovered as a liquid from the downstream side of the film.

Composite membranes prepared by interfacial crosslinking have been used in various processes including water purification, reverse osmosis, organic/organic separations, gas/liquid separation, etc. In such processes, the charge/retentate side of the membrane is commonly at a high pressure (typically 700 psig) and the permeate side of the membrane is commonly at atmospheric pressure. The permeate is recovered in liquid phase.

Illustrative of such processes are those set forth in the following patents:

U.S. Pat. No. 5,037,555 to Texaco Inc as assignee of Mordechai Pasternak and Abraham Morduchowitz is directed to desalination of water by reverse osmosis across a membrane of a polyimine polymer which has been cross-linked with an isocyanate or a carbonyl chloride cross-linking agent.

U.S. Pat. No. 4,865,745 to Texaco Inc as assignee of Mordechai Pasternak is directed to dewatering of dilute aqueous solutions of organic oxygenates by a pressure driven process across a membrane of a polyimine polymer which has been crosslinked with an isocyanate or a carbonyl chloride cross-linking agent.

U.S. Pat. No. 4,897,091 to Texaco Inc as assignee of Mordechai Pasternak and Richard Beaupre is directed to separation of carbon dioxide from solution thereof in methanol by use in a pressure driven process, of a membrane which is the reaction product of (i) a polyamine and (ii) a polyisocyanate or a poly (carbonyl chloride).

U.S. Pat. No. 4,985,138 to Texaco Inc as assignee of Mordechai Pasternak is directed to separation of dewaxed oil from dewaxing solvent by a pressure driven process across a polyurea membrane.

There is also a body of prior art directed to separation of water from dilute solutions of various compositions by pervaporation wherein the permeate is recovered in vapor phase under vacuum. Illustrative of such processes are those set forth in the following patents:

U.S. Pat. No. 4,802,988 to Texaco Inc as assignee of John Reale, Jr. and Craig R. Bartels is directed to separation of water from ethylene glycol by pervaporation across a membrane of polyvinyl alcohol which has been cross-linked with an aliphatic polyaldehyde containing at least three carbon atoms.

U.S. Pat. No. 5,004,861 to Texaco Inc as assignee of Mordechai Pasternak, Craig R. Bartels, and John Reale, Jr. is directed to separation of water from a charge mixture of hydrocarbon and organic oxygenate by use, in a pervaporation process, of (i) a membrane of polyvinyl alcohol which has been cross-linked with a polyaldehyde containing at least three carbon atoms or (ii) a composite membrane of blended polyvinyl alcohol and polyacrylic acid.

U.S. Pat. No. 4,935,144 to Texaco Inc as assignee of Mordechai Pasternak, Craig R. Bartels, and John Reale, Jr. is directed to separation of aqueous solutions of organic oxygenates by pervaporation across a membrane of polyvinyl alcohol which has been cross-linked with a polyaldehyde containing at least three carbon atoms.

U.S. Pat. No. 4,910,344 to Texaco Inc as assignee of Mordechai Pasternak, Craig R. Bartels, and John Reale, Jr. is directed to separation of water from a charge mixture of hydrocarbon and organic oxygenates by pervaporation across a composite membrane of polyvinyl alcohol and a polyarcylic acid.

U.S. Pat. No. 4,992,176 to Texaco Inc as assignee of Craig R. Bartels is directed to dehydration of organic oxygenates by pervaporation through a membrane of dibromo butane-cross-linked polyvinyl pyridine.

U.S. Pat. No. 5,032,278 to Texaco Inc as assignee of John Reale, Jr. is directed to dehydration of hydrocarbon/organic oxygenate mixtures by pervaporation across a heat-treated polyethylene imine membrane.

Additional background may be obtained from (i) U.S. Pat. No. 4,411,787 to UOP as assignee of Riley; (ii) J. E. Cadotte et al, J. Macromol. Sci-Chem A15 (5) p 727 (19810; (iii) L. T. Rozelle et al Chapter 1 in *Reverse Osmosis and Synthetic Membranes* S. Sourirajan (Ed). See also the references cited in the above patents.

U.S. application Ser. No. 07/553,512, filed Jul. 16, 1990 by Texaco Inc as assignee of Mordechai Pasternak disclose separation of dewaxing solvent from dewaxed oil, by a pressure driven process, across as a separating membrane, a non-porous polyurea formed by the reaction of (i) a compound containing at least two isocyanate groups and (ii) a compound containing at least two amine groups.

It is an object of this invention to provide a process for dewatering aqueous solutions. Other objects will be apparent to those skilled in the art.

STATEMENT OF THE INVENTION

In accordance with certain of its aspects, this invention is directed to a method which comprises passing a charge aqueous solution of an organic oxygen-containing liquid component which is soluble in water into contact with, as pervaporation membrane, a non-porous separating layer of polyurea polymer or polyamide polymer prepared by interfacial polymerization of (i) an amine monomer containing at least two primary or secondary amine nitrogens and (ii) an isocyanate monomer containing at least two —NCO groups or a carbonyl chloride monomer containing at least two—COCl groups;

maintaining a pressure drop across said membrane thereby forming a high pressure retentate containing increased content of organic oxygen-containing component and decreased content of water and a low pressure permeate of increased content of water and decreased content of organic oxygen-containing component;

maintaining the pressure on the low pressure discharge side of said membrane below the vapor pressure of said permeate thereby maintaining said permeate in vapor phase;

maintaining the pressure on the high pressure retentate side of said membrane above the vapor pressure of said charge aqueous solution and of said retentate thereby maintaining said charge aqueous solution and said retentate in liquid phase;

recovering said permeate of increased content of water and decreased content of organic oxygen-containing component, in vapor phase from the low pressure discharge side of said membrane; and recovering said retentate of increased content of organic oxygen-containing component and decreased content of water, in liquid phase from the high pressure side of said membrane.

DESCRIPTION OF THE INVENTION THE CHARGE SOLUTION

The charge aqueous solution of organic oxygen-containing liquid component which may be treated by the process of this invention may include oxygen-containing compounds such as alcohols, glycols, organic carboxylic acids, polyols, aldehydes, ketones, etc. When the oxygen-containing component is an alcohol, it maybe for example ethanol, propanol, isopropanol, n-butanol, isobutanol, t-butanol, hexanols, octanols, etc. When the oxygen-containing component is a glycol it may be for example ethylene glycol, propylene glycol, butylene glycol, etc. When the oxygen-containing component is a polyol, it maybe for example glycerine, sorbitol, pentaerythritol, trimethylolmethane, polyoxyethylene (or polyoxypropylene) polyol, etc. When the oxygen-containing component is an acid, it may for example be acetic acid, propionic acid, butyric acid, etc. When the oxygen-containing component is an aldehyde, it may for example be formaldehyde, acetaldehyde, etc. When the oxygen-containing component is a ketone, it may for example be acetone, methyl ethyl ketone, acetophenone, etc.

It is a particular feature of the process of this invention that the advantages thereof may be most readily apparent when the charge aqueous solution is a concentrated aqueous solution.

It is also possible to utilize the process of this invention with immiscible mixtures or with partially miscible mixtures.

Although the advantages may be attained when the charge concentrated solution contains less than say 70 w % or more of organic oxygen-containing component, it may be found that desired results are be obtained when the charge solutions are at or above the 90 w % level. It is particularly found that desired results may be attained when the charge contains 95 w %-98 w % oxygenate.

The instant process may find particular use in connection with other concentration techniques. For example, a particular charge solution may be concentrated by distillation up to a point at which further concentration by distillation maybe uneconomical. A charge may, for example, be concentrated to a point at which an azeotrope is formed. In alternative aspects, the process of the instant invention may be employed first, followed, for example, by distillation. Clearly in each case the number of separation steps and the particular sequence will depend on the economics of the particular system which of course depend on the composition and properties of the charge solution.

The process of this invention is found to be particularly useful in treating charge solutions containing ethyl alcohol (in concentration of 95 w %) or isopropanol (in concentration of say 85 w %) to recover product containing decreased quantities of water.

Illustrative charge solutions which may be employed in practice of the process of this invention may include:

| | |
|---|---|
| (i) | 95 w % ethyl alcohol |
| | 5 w % water |
| (ii) | 80 w % ethylene glycol |
| | 20 w % water |
| (iii) | 95 w % ethylene glycol |
| | 5 w % water |
| (iv) | 95 w % acetone |
| | 5 w % water |
| (v) | 92 w % acetic acid |
| | 8 w % water |
| (vi) | 75 w % acetaldehyde |
| | 25 w % water |
| (vii) | 85 w % isopropanol |
| | 15 w % water |

THE MEMBRANE ASSEMBLY

Practice of the process of this invention may be carried out by use of a composite structure which in one preferred embodiment may include (i) a carrier layer which provides mechanical strength, (ii) a porous support layer, and (iii) a separating layer across which separation occurs.

The composite structure of this invention includes a multi-layer assembly which in the preferred embodiment, preferably includes a porous carrier layer which provides mechanical strength and support to the assembly.

THE CARRIER LAYER

This carrier layer is characterized by its high degree of porosity and mechanical strength. It may be fibrous or non-fibrous, woven or non-woven. In the preferred embodiment, the carrier layer may be a porous, flexible, non-woven fibrous polyester.

A preferred non-woven polyester carrier layer may be formulated of non-woven, thermally-bonded strands of polyester and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cu. ft/min. sq. ft.@0.5 inches of water.

THE POROUS SUPPORT LAYER

The porous support layer useful in practice of the process of this invention may be preferably formed of an ultrafiltration membrane—preferably formed of polyacrylonitrile polymer. Typically the polyacrylonitrile may be of thickness of 40–80 microns, say 50 microns and is preferably characterized by a pore diameter of less than about 500A and typically about 200 A. This corresponds to a molecular weight cut-off less than about 50,000, typically about 40,000. A preferred commercially available porous support layer is the Daicel DUY-L brand of polyacrylonitrile (molecular weight cut-off of about 40,000) which is available on a non-woven, thermally bonded polyester carrier layer of polyester.

In another embodiment, the porous support layer may be formed of a sheet of polysulfone polymer. Typically the polysulfone may be of thickness of 40–80 microns, say 50 microns and of molecular weight $M_n$ of 5,000–100,000, preferably 20,000–60,000 say 40,000. The polysulfone is preferably characterized by a pore size of about 100 A. This corresponds to a molecular weight cut-off of about 20,000.

The sulfone polymers which may be employed may include those made from cumene containing isopropylidene groups in the backbone; e.g.

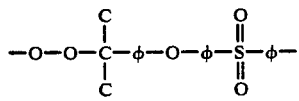

These isopropylidene sulfones, containing as repeating units ether-aromatic-isopropylidene-aromatic-ether aromatic-sulfone-aromatic groups, may typically have a molecular weight 15,000–30,000, water absorption (at 20° C.) of about 0.85 w %, a glass transition temperature of 449° K, a density of 1.25 mg/m³, a tensile strength (at 20° C.) at yield of 10,000 psi, and a coefficient of linear thermal expansion of $1.6 \times 10^{-5}$ mm/mm/°C.

THE SEPARATING LAYER

The separating layer which permits attainment of separation in accordance with the process of this invention includes a non-porous film or membrane of 0.2–1 microns, say about 0.5 microns of a polyurea or a polyamide.

The separating layer may preferably be a layer of polyurea polymer or polyamide polymer prepared by interfacial polymerization of (i) an amine monomer containing at least two primary or secondary amine nitrogens and (ii) an isocyanate monomer containing at least two —NCO groups or a carbonyl chloride monomer containing at least two —COCl groups.

$$R''(NHR)_c \text{ and } R''[(NCO)_a(COCl)_{1-a}]_b$$

wherein
R is a monovalent hydrocarbon moiety;
R" is a polyvalent hydrocarbon moiety;
a is 0 or 1; and
b and c are integers greater than 1.

The first reactant R" (HRC)$_c$ is a polyamine (i.e. a preferably monomeric compound containing a plurality of amine groups). In this compound, c may be an integer greater than one. When c is two, the first reactant is a diamine.

R" may be a polyvalent hydrocarbon moiety such as in 1,3,5-benzene tri(carbonyl chloride). In the preferred embodiment, R" may be a divalent moiety.

In the above formula, R" may preferably be a hydrocarbon group selected from the group consisting of alkylene, aralkylene, cycloalkylene, arylene, and alkarylene, including such radicals when inertly substituted. When R" is alkylene, it may typically be methylene, ethylene, n-propylene, iso-propylene, n-butylene, i-butylene, sec-butylene, amylene, octylene, decylene, octadecylene, etc. When R" is aralkylene, it may typically be benzylene, beta-phenylethylene, etc. When R" is cycloalkylene, it may typically be cyclohexylene, cycloheptylene, cyclooctylene, 2-methylcycloheptylene, 3-butylcyclohexylene, 3-methylcyclohexylene, etc. When R" is arylene, it may typically be phenylene, naphthalene, etc. When R" is alkarylene, it may typically be tolylene, xylylene, etc. R" may be inertly substituted i.e. it may bear a non-reactive substituent such as alkyl, aryl, cycloalkyl, ether, etc. Typically inertly substituted R" groups may include 3-methoxypropylene, 2-ethoxyethylene, carboethoxymethylene, 4-methylcyclohexylene, p-methylphenylene, p-methylbenzylene, 3-ethyl-5-methylphenylene, etc. The preferred R" groups may be phenylene or lower alkylene, i.e. $C_1$–$C_{10}$ alkylene, groups including e.g. methylene, ethylene, n-propylene, i-propylene, butylene, amylene, hexylene, octylene, decylene, etc. R" may preferably be phenylene or hexamethylene.

In the above compound, R may be a hydrocarbon group selected from the group consisting of alkyl, aralkyl, cycloalkyl, aryl, and including such radicals when inertly substituted. When R is alkyl, it may typically be methyl, ethyl, n-propyl, iso-propyl, n-butyl, i-butyl, sec-butyl, amyl, octyl, decyl, octadecyl, etc. When R is aralkyl, it may typically be benzyl, beta-phenylethyl, etc. When R is cycloalkyl, it may typically be cyclohexyl, cycloheptyl, cyclooctyl, 2-methylcycloheptyl, 3-butylcyclohexyl, 3-methylcyclohexyl, etc. When R is aryl, it may typically be phenyl, naphthyl, etc. When R is alkaryl, it may typically be tolyl, xylyl, etc. R may be inertly substituted i.e. it may bear a non-reactive substituent such as alkyl, aryl, cycloalkyl, ether, etc. Typical inertly substituted R groups may include 3-methoxypropyl, 2-ethoxyethyl, carboethoxymethyl, 4-methylcyclohexyl, p-methylphenyl, p-methylbenzyl, 3-ethyl-5-methylphenyl, etc. The preferred R groups may be lower alkyl, i.e. $C_1$–$C_{10}$ alkyl, groups including e.g. methyl, ethyl, n-propyl, i-propyl, butyls, amyls, hexyls, octyls, decyls, etc. R may preferably be hydrogen.

In one of its preferred embodiments, the R" group of the first amine monomer reactant may contain a polyoxyalkylene moiety or a polyalkylene imine moiety. Illustrative of the amine monomers may be those set forth in the following table, the first listed being preferred:

TABLE

A. diethylene triamine
B. triethylene tetramine
C. m-phenylenediamine
D. piperazine The amine monomer containing at least two primary or secondary amine groups may be preferably selected from one of the following groups;

$$H_2N-R''+NH-R\}_n NH_2 \quad (i)$$

typified by:

TABLE

| diethylene | triamine |
|---|---|
| triethylene | tetramine |

(ii)
$$H_2N-R''+OR''\}_a NH_2$$

typified by $$H_2N-C_2H_4+OC_2H_4+NH_2$$
$$H_2N-C_2H_4+OC_2H_4\}_7 NH_2$$
$$H_2N-C_3H_8+OC_2H_4\}_7 NH_2$$

Illustrative commercially available compositions may include
(i) the Jeffamine ED-600 brand of poly (oxyethylene) diamine of $\overline{M}n$ of 900; and
(ii) the Jeffamine D-400 brand of poly (oxyethylene) diamine of $\overline{M}n$ of 400.
(iii) R" $(NH_2)_b$
typified by:

TABLE p-phenylene diamine
1,3-diamopropane (iv) heterocyclics containing at least one nitrogen in the ring typified by

TABLE piperazine
p-amino pyridine

Other categories of amine monomers containing at least two primary or secondary amine groups may include compounds typified by:

$$\begin{array}{c} CH_2(OCH_2-CH)_x NH_2 \\ | \\ CH_3 \\ CH_3-CH_2-C-CH_2(OCH_2CH)_y NH_2 \\ | \\ CH_3 \\ CH_2-(OCH_2-CH)_z NH_2 \\ | \\ CH_3 \end{array}$$

wherein $x+y+z=5.3$ etc.

The second monomer reactant $$R''+(NCO)_a(COCl)_{1-a}\}_b$$

wherein a is 0 and 1 and b is an integer greater than 1, may be a polyisocyanate monomer when a is 1. When a i 0, the second reactant may be a poly(carbonyl chloride) monomer. Preferably a is 1 and b is 2 i.e. the preferred second reactant is a diisocyanate.

R" in the second monomer reactant may be selected from the same group as that from which R" in the first amine monomer reactant is selected. In the preferred embodiment, R" in the first reactant may be different from the R" in the second reactant; and preferably at least one of the R" groups is aromatic.

The preferred polyisocyanates (i.e. monomeric compounds bearing a plurality of —NCO isocyanate groups) may include those which contain an aromatic nucleus, typically a toluene diisocyanate or a phenylene diisocyanate.

The preferred poly(carbonyl chlorides) i.e. monomeric compounds bearing a plurality of —COCl carbonyl chloride groups) may include those which contain an aromatic Illustrative second monomer reactants may include the following, the first listed being preferred:

TABLE 1,3,5-benzene tri(carbonyl chloride)
suberoyl dichloride
meta-phenylene diisocyanate
2,4-toluene diisocyanate
3,5-toluene diisocyanate
para-phenylene diisocyanate
hexamethylene diisocyanate
isophthaloyl dichloride
terephthaloyl dichloride In practice of the process of this invention, the separating membrane layer may be prepared by interfacial polymerization. This may be effected as by casting the membrane on a support layer, such as the preferred porous polyacrylonitrile support. In this aspect of the invention, one of the reactants, preferably the first reactant (e.g. diethylene triamine in 2-3 w % aqueous solution) is poured onto a support membrane over 1-8 minutes, say 2 minutes. The membrane is then held in vertical position for 1 minute to drain excess solution.

The second reactant (e.g. 2,4-toluene diisocyanate) preferably in 1% solution in a hydrocarbon such as hexane is then poured on in equivalent amount carefully onto the surface of the support membrane into which the first reactant has been absorbed. The first and second reactants are allowed to interfacially polymerize at 20°–30° C. for 20–60 seconds, say 20 seconds. The excess of unreacted second reactant may the be carefully poured off to terminate the interfacial reaction process. The so-formed assembly may be heat cured at 110° C.–140° C., say 110° C. for 10–30 minutes, say 15 minutes. During this curing, thermal cross-linking may complete the fabrication of the barrier layer.

THE COMPOSITE MEMBRANE

It is a feature of this invention that it may utilize a composite membrane which comprises (i) a carrier layer characterized by porosity and mechanical strength, for supporting a porous support layer, (ii) preferably a porous support layer such as a polyacrylonitrile membrane of thickness of 40–80 microns, and of molecular weight cut-off of 25,000–50,000, and (iii) a non-porous separating layer of polyurea or polyamide prepared by interfacially polymerization of an amine monomer containing at least two primary or secondary amine nitrogens and an isocyanate monomer containing at least two —NCO groups or a carbonyl chloride monomer containing at least two —COCl groups.

It is possible to utilize a spiral wound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the perforations of the conduit; and the bag-like unit is wrapped around the conduit to form a spiral wound configuration. It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell (in manner comparable to a shell-and-tube heat exchanger) provided with an inlet at one end and an outlet at the other. A baffle like seal between the inner surface of the shell and the outer surface of the spiral-wound unit prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The vapor which permeates the membrane passes into the volume occupied by the permeate spacer and through this permeate channel to the perforations in the cylindrical conduit through which it is withdrawn from the system. It is possible to utilize a spiral wound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There then placed on one face of the bag-like unit, adjacent to the separating layer, and coterminous therewith, a feed channel sheet—typically formed of a plastic net.

In another embodiment, it is possible to utilize the system of this invention as a tubular or hollow fiber. In this embodiment, the polyacrylonitrile porous support layer may be extruded as a fine tube with a wall thickness of typically 0.001–0.1 mm. The extruded tubes are passed successively of these tubes is secured (with an epoxy adhesive) at each end in a header; and the fibers are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

PERVAPORATION

It is a feature of the non-porous cross-linked separating layer that it is found to be particularly effective when used in a pervaporation process. In pervaporation, a charge liquid containing a more permeable and a less permeable component is maintained in contact with a non-porous separating layer; and a pressure drop is maintained across that layer. The permeate side is maintained at a pressure below the vapor pressure of the permeate—typically at about 1 mm.Hg. A portion of the charge liquid dissolves into the membrane and diffuses therethrough. The permeate passes through the membrane and exits as a vapor.

It is a feature of this invention that the membrane may be particularly useful in pervaporation processes for treatment of aqueous solutions.

In practice of the process of this invention, the charge aqueous in liquid phase typically at 40° C.–80° C., say 70° C. may be passed into contact with the non-porous separating layer of the interfacially polymer membrane of this invention. A pressure drop is commonly maintained across the membrane. The feed or charge side of the membrane is typically at atmospheric pressure; and the permeate or discharge side of the membrane is at pressure below the vapor pressure of the permeate—typically 1–50 mmHg, say about 1 mm.Hg.

The permeate which passes through the membrane includes water and a substantially decreased concentration of organic from the charge liquid. Typically, the permeate contains 80–100, say 99 w % water. Permeate is recovered in vapor phase.

Pervaporation may typically be carried out at a flux of 0.5–3, say 1.3 kilograms per square meter per hour. Typically, the Selectivity may be more than 75% and typically 75–99 w %, say as high as 99+w % water in permeate.

Practice of the process of this invention will be apparent to those skilled in the art from inspection of the following examples wherein, as elsewhere in this specification, all parts are parts by weight unless otherwise stated.

DESCRIPTION OF SPECIFIC EMBODIMENTS

Example I

In this Example, which represents the best mode presently known of carrying out the process of this invention, the carrier layer is a non-woven layer of thermally bonded strands of polyester characterized by a fabric weight of 80±8 grams per square yard, a thickness of 4.2±0.5 mils, a tensile strength (in mechine direction) of 31 psi and (in cross direction) of 10 psi, and a Frazier air permeability of 6 cu. ft/min./sq. ft @0.5 inches of water. The porous support layer is a commercially available layer of Daicel DUY-L brand of poly acrylonitrile (of molecular weight cut-off of about 40,000) bonded thereto.

The Selective separation membrane is prepared by mixing a 3 w % solution in water of triethylene tetramine and a 1 w % solution in hexane of 2,4-toluene diisocyanate for 20 seconds. At the end of the interfacial polymerization reaction, the excess is poured off the porous support layer. The assembly is then heat cured at 110° C. for 15 minutes.

The membrane assembly so prepared is mounted in a standard pervaporation cell. Charge and retentate pressure is atmospheric. Permeate pressure are Ca 1 mm.

Hg. Permeate is recovered as vapor and condensed against liquid nitrogen.

There is charged to this pervaporation cell a charge solution at 70° C. containing 85 w % isopropanol and 15 w % water. The Selectivity (i.e. percent water in the permeate) is 99.3 w %; and the Flux is 1.11 kilograms/-square meter/hour (kmh).

Example II

The procedure of Example I is duplicated except that, in place of the triethylene tetramine, there is employed 3% diethylene triamine.

Selectivity is 94.8 w %. Flux is 0.99 kmh.

Example III

In this Example, the membrane preparation procedure of Example I is duplicated.

There is charged to the membrane assembly at 80° C. a charge solution containing 95 w % ethanol and 5 w %

Selectivity is 99 w %. Flux is 0.66 kmh.

Example IV

In this Example, the membrane preparation procedure of Example II is duplicated. The charge solution is the same as that of Example III.

Selectivity is 99 w %. Flux is 0.52 kmh.

In Examples V-IX, the charge solution at 80° C. contains 95 w % ethanol and 5 w % water.

Example V

In this Example, the membrane preparation procedure of Example I is duplicated except that the amine is 3% m-phenylene diamine in water.

Selectivity is 84.9 w %. Flux is 0.24 kmh.

Example VI

In this Example, the membrane preparation procedure of Example II is duplicated except that the amine is 3 w % piperazine in water.

Selectivity is 81.3 w %. Flux is 0.56 kmh.

Example VII

In this Example the membrane preparation procedure of Example II is duplicated except that in place of toluene diisocyanate there is employed 2 w % isophthaloyl chloride in hexane and the membrane is cured at 125° C.

Selectivity is 97 w %. Flux is 0.59 kmh.

Example VIII

In this Example, the procedure of Example VII is duplicated except that in place of isophthaloyl chloride, there is employed 2 w % hexamethylene diisocyanate in hexane. Interfacial reaction occurs over 30 seconds.

Selectivity 76.1 w %. Flux is 1.34 kmh.

Example IX

In this Example, the procedure of Example I is duplicated except that:

(i) in place of 3 w % solution of triethylene tetramine, there is employed 3 w % solution of the Jeffamine T-403 brand of:

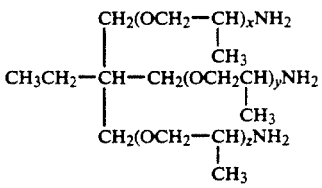

wherein $x+y+z$ is 5.3.

Selectivity is 91.5 w %. Flux is 0.89 kmh.

In Examples X and XI, the charge is 95 w % acetone and 5% w water.

Example X

In this Example, the procedure of Example I is duplicated.

Selectivity is 88.7 w %. Flux is 1.29 kmh.

Example XI

In this Example, the procedure of Example II is duplicated.

Selectivity is 97.7 w %. Flux is 1.29 kmh.

Results comparable to those of Example I maybe attained if the charge solution is:

TABLE

| Example | Charge Solution |
|---|---|
| XII | 80 w % isopropanol |
|  | 20 w % water |
| XIII | 95 w % ethylene glycol |
|  | 5 w % water |
| XIV | 92 w % acetic acid |
|  | 8 w % water |
| XV | 75 w % acetaldehyde |
|  | 25 w % water |

Results comparable to those of Example I may be attained if the amine reactant is:

| Example | Amine Reactant |
|---|---|
| XVI | p-phenylene diamine |
| XVII | 1,5-pentane diamine |
| XVIII | 1,6-hexane diamine |
| XIX | pentaethylene hexamine |
| XX | 1,4-butane diamine |

Results comparable to those of Example I may be attained if the isocyanate reactant is:

| Example | Isocyanate Reactant |
|---|---|
| XXI | m-phenylene diisocyanate |
| XXII | p-phenylene diisocyanate |

Results comparable to those of Example I may be attained if, in place of the isocyanate reactant, the following carbonyl chloride reactants are employed:

| Example | Carbonyl Chloride Reactant |
|---|---|
| XXIII | suberoyl dichloride |
| XXIV | 1,3,5-benzene tri(carbonyl chloride) |

Although this invention has been illustrated by reference to specific embodiments, it will be apparent to those skilled in the art that various charges and modifications may be made which clearly fall within the scope of the invention.

What is claimed:

1. The method which comprises
    passing a charge aqueous solution of an organic oxygen-containing liquid component which is soluble in water into contact with, as pervaporation membrane, a non-porous separating layer of polyurea polymer or polyamide polymer prepared by interfacial polymerization of (i) an amine monomer containing at least two primary or secondary amine nitrogens and (ii) an isocyanate monomer containing at least two —NCO groups or a carbonyl chloride monomer containing at least two —COCl groups;
    maintaining a pressure drop across said membrane thereby forming a high pressure retentate containing increased content of organic oxygen-containing component and decreased content of water and a low pressure permeate of increased content of water and decreased content of organic oxygen-containing component;
    maintaining the pressure on the low pressure discharge side of said membrane below the vapor pressure of said permeate thereby maintaining said permeate in vapor phase;
    maintaining the pressure on the high pressure retentate side of said membrane above the vapor pressure of said charge aqueous solution and of said retentate thereby maintaining said charge aqueous solution and said retentate in liquid phase;
    recovering said permeate of increased content of water and decreased content of organic oxygen-containing component, in vapor phase from the low pressure discharge side of said membrane; and
    recovering said retentate of increased content of organic oxygen-containing component and decreased content of water, in liquid phase from the high pressure side of said membrane.

2. The method of claim 1 wherein said charge organic oxygen-containing component is an alcohol, a glycol, an organic carboxylic acid, a polyol, an organic carboxylic acid, a polyol, an aldehyde, or a ketone.

3. The method of claim 1 wherein said charge organic oxygen-containing component is an alcohol.

4. The method of claim 1 wherein said charge organic oxygen-containing component is isopropanol.

5. The method of claim 1 wherein said charge organic oxygen-containing component is a glycol.

6. The method of claim 1 wherein said charge organic oxygen-containing component is ethylene glycol.

7. The method of claim 1 wherein said charge organic oxygen-containing component is an organic carboxylic acid.

8. The method of claim 1 wherein said charge organic oxygen-containing component is a polyol.

9. The method of claim 1 wherein said charge organic oxygen-containing component is an aldehyde.

10. The method of claim 1 wherein said charge organic oxygen-containing component is a ketone.

11. The method of claim wherein said isocyanate monomer is a diisocyanate.

12. The method of claim 1 wherein said isocyanate monomer is toluene diisocyanate.

13. The method of claim wherein said isocyanate monomer is phenylene diisocyanate.

14. The method of claim 1 wherein said carbonyl chloride monomer is a di(carbonyl chloride).

15. The method of claim 1 wherein said carbonyl chloride monomer is suberoyl dichloride.

16. The method of claim 1 wherein said carbonyl chloride monomer is isophthaloyl dichloride.

17. The method which comprises
    passing a charge aqueous solution containing 95 w % ethyl alcohol into contact with, as a pervaporation membrane, a non-porous separating layer which is the reaction product of triethylene tetramine and 2,4-toluene diisocyanate;
    maintaining a pressure drop across said membrane thereby forming a high pressure retentate containing increased content of ethyl alcohol and decreased content of water and a low pressure permeate of increased content of water and decreased content of ethyl alcohol;
    maintaining the pressure on the low pressure discharge side of said membrane below the vapor pressure of said permeate thereby maintaining said permeate in vapor phase;
    maintaining the pressure on the high pressure retentate side of said membrane above the vapor pressure of said charge aqueous dilute solution and of said retentate thereby maintaining said charge aqueous dilute solution and said retentate in liquid phase;
    recovering said permeate of increased content of water and decreased content of ethyl alcohol, in vapor phase, from the low pressure discharge side of said membrane; and
    recovering said retentate of increased content of ethyl alcohol and deceased content of water, liquid phase, from the high pressure side of said membrane.

* * * * *